(12) United States Patent
Fujii et al.

(10) Patent No.: US 11,402,810 B2
(45) Date of Patent: Aug. 2, 2022

(54) LEARNING DEVICE AND CUTTING PROCESS EVALUATION SYSTEM

(71) Applicant: Panasonic Intellectual Property Management Co., Ltd., Osaka (JP)

(72) Inventors: Keitaro Fujii, Osaka (JP); Masayuki Takahashi, Osaka (JP); Tosihiko Wada, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 343 days.

(21) Appl. No.: 16/750,034

(22) Filed: Jan. 23, 2020

(65) Prior Publication Data
US 2020/0254501 A1 Aug. 13, 2020

(30) Foreign Application Priority Data

Feb. 7, 2019 (JP) .............................. JP2019-020615
Jan. 8, 2020 (JP) .............................. JP2020-001388

(51) Int. Cl.
*G05B 13/02* (2006.01)
*G05B 13/04* (2006.01)
(Continued)

(52) U.S. Cl.
CPC ........ *G05B 13/042* (2013.01); *A22C 17/0086* (2013.01); *B21D 28/34* (2013.01);
(Continued)

(58) Field of Classification Search
CPC .. A61B 17/3496; H01R 43/0486; H02K 7/14; G06N 20/00; G06N 3/084; G06N 3/0454; A22C 17/0086; B23Q 17/0985; B23Q 17/12; G05B 13/021; G05B 17/02; G05B 13/042; G06K 9/6297
See application file for complete search history.

(56) References Cited

U.S. PATENT DOCUMENTS

| 10,776,691 | B1* | 9/2020 | Ghahramani | .......... G06N 3/084 |
| 2003/0088322 | A1* | 5/2003 | Martin | .................. G05B 17/02 |
| | | | | 700/52 |

(Continued)

FOREIGN PATENT DOCUMENTS

| JP | 6-079500 | 3/1994 |
| JP | 6-304800 | 11/1994 |

(Continued)

OTHER PUBLICATIONS

Li et al., "Based on Vector Imaging Model of Low-error Sensititivy Target Light Source-mask Optimization method", CN 106125511 (translation), Nov. 21, 2017 < CN_106125511.pdf>.*

Primary Examiner — Tuan A Vu
(74) Attorney, Agent, or Firm — Wenderoth, Lind & Ponack L.L.P.

(57) ABSTRACT

A learning device includes an input processor and a learning processor. The input processor acquires a physical quantity related to a cutting process, and inputs a state variable based on the physical quantity to the learning processor, and the learning processor updates, based on a measured cutting result, an evaluation model that outputs an evaluation result of the cutting process based on the state variable.

4 Claims, 9 Drawing Sheets

(51) Int. Cl.
  *B21D 28/34* (2006.01)
  *G06N 20/00* (2019.01)
  *B23Q 17/09* (2006.01)
  *B23Q 17/12* (2006.01)
  *A22C 17/00* (2006.01)
  *A61B 17/34* (2006.01)

(52) U.S. Cl.
  CPC ......... *B23Q 17/0985* (2013.01); *B23Q 17/12* (2013.01); *G05B 13/021* (2013.01); *G06N 20/00* (2019.01); *A61B 17/3496* (2013.01)

(56) References Cited

U.S. PATENT DOCUMENTS

| | | | |
|---|---|---|---|
| 2004/0007041 A1* | 1/2004 | Imgrut | H01R 43/0486 72/412 |
| 2006/0095059 A1* | 5/2006 | Bleich | A61B 17/3496 606/170 |
| 2008/0228680 A1* | 9/2008 | Chen | G06N 3/0454 706/21 |
| 2010/0020208 A1* | 1/2010 | Barbu | G06K 9/6297 348/E5.079 |
| 2017/0228644 A1 | 8/2017 | Kurokawa | |
| 2017/0277174 A1 | 9/2017 | Maeda | |
| 2017/0357243 A1 | 12/2017 | Takayama et al. | |
| 2020/0068909 A1* | 3/2020 | Blaine | A22C 17/0086 |
| 2020/0166909 A1* | 5/2020 | Noone | G06N 20/00 |
| 2020/0276680 A1* | 9/2020 | Green | H02K 7/14 |

FOREIGN PATENT DOCUMENTS

| | | |
|---|---|---|
| JP | 7-021216 U | 4/1995 |
| JP | 2017-138881 | 8/2017 |
| JP | 2017-174236 | 9/2017 |
| JP | 2017-220111 | 12/2017 |

\* cited by examiner

FIG. 11

| Label | Tool wear | Chipping (maximum width) | Burr height | Clogging | Clearance deviation |
|---|---|---|---|---|---|
| 1(No abnormality) | Less than R20 μm | Less than 5 μm | Less than 15 μm | No | Less than 1 μm |
| 2 (Yellow signal) | R20 μm or more Less than R25 μm | 5 μm or more Less than 10 μm | 15 μm or more Less than 20 μm | – | 1 μm or more Less than 2 μm |
| 3(Abnormality) | R25 μm or more | 10 μm or more | 20 μm or more | Yes | 2 μm or more |

LEARNING DEVICE AND CUTTING PROCESS EVALUATION SYSTEM

BACKGROUND

1. Technical Field

The present disclosure relates to a learning device used in an evaluation system for a workpiece manufactured by a cutting process and a cutting process evaluation system using the same.

2. Description of the Related Art

In a cutting process, generally, a predetermined shape is obtained by pressing a workpiece placed on a member called a die with a member called a stripper and pushing the workpiece into the die to punch it with a tool called a punch. The cutting process is generally used in a wide variety of manufacturing fields, such as home appliance manufacturing, precision instrument manufacturing, or automobile parts manufacturing.

In such a cutting process using the die, it is common to adjust a position or shape of the mold by trial and error according to the individual mold (die), but there are cases that cannot be handled with the adjustment by trial and error, and in such a case, a processed product with a predetermined quality cannot be obtained. Therefore, like an evaluation method disclosed in Japanese Patent Unexamined Publication No. H6-304800, the evaluation method is proposed in which a physical quantity generated by a cutting process is measured, and an abnormality diagnosis is performed by comparing the measured value of the physical quantity with a reference value.

Further, as a quality determination of a processed product in a general processing apparatus, like an evaluation method disclosed in Japanese Patent Unexamined Publication No. 2017-174236, the evaluation method is proposed in which a quality determination is performed by comparing a measured value of internal information of a processing apparatus with a threshold set in a temporary determination unit, and the quality of the actual processed product is fed back to update the threshold of the temporary determination unit.

SUMMARY

A learning device according to the present disclosure includes an input processor and a learning processor. The input processor acquires a physical quantity related to a cutting process, and inputs a state variable based on the physical quantity to the learning processor, and the learning processor updates, based on a measured cutting result, an evaluation model that derives an evaluation of the cutting process based on the state variable.

BRIEF DESCRIPTION OF THE DRAWINGS

FIG. 11 is a diagram showing an example of cutting result input to a learning device according to the embodiment of the present disclosure.

DETAILED DESCRIPTION

In the evaluation method disclosed in Japanese Patent Unexamined Publication No. H6-304800, a reference for determining whether or not the process is normal is whether or not the acquired value (measured value) falls within an acceptable range (allowable range) with respect to the value obtained from the normal process (reference value). Therefore, the setting of the allowable range needs to be examined each time according to the specifications of the workpiece and the processed product. In addition, in the evaluation method disclosed in Japanese Patent Unexamined Publication No. H6-304800, even if an abnormality can be detected, the cause of the abnormality cannot be specified, so that it takes time to deal with the abnormality.

The evaluation method disclosed in Japanese Patent Unexamined Publication No. 2017-174236 has the following problems. In other words, in general, there is a fracture mechanics aspect in cutting process where fracture separation occurs after crack growth occurs from compressive deformation to plastic deformation, and the fracture process is performed in an extremely short time of 0.1 second or less. Therefore, for example, it is not possible to grasp the state of the fracture process such as the load profile at the time of fracture separation with internal information such as the current value and rotation speed of the motor, and it is difficult to obtain the necessary number of data samples within a short time. Therefore, it is difficult to accurately determine the quality of the processing process (and thus the quality of the processed product) based only on the internal information of the processing apparatus.

The present disclosure has been made in view of the problems of the above related art, and an object thereof is to make it possible to accurately evaluate a cutting process.

Hereinafter, Embodiment 1 of the present disclosure will be described with reference to FIGS. 1 to 10.

Figure 1:
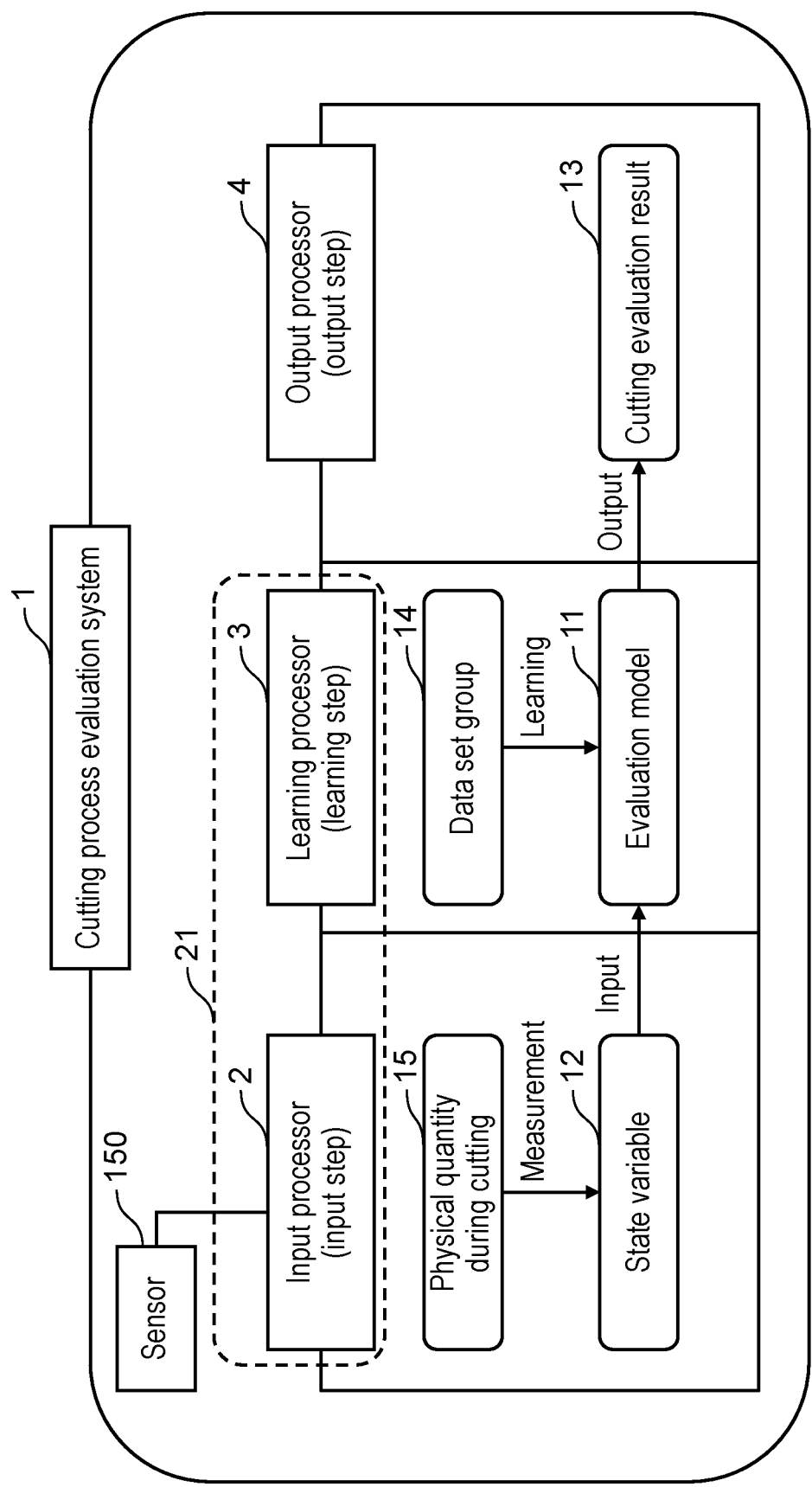
FIG. 1 is a block principle diagram showing an outline of a cutting process evaluation system used in an embodiment of the present disclosure.

FIG. 1 is a block principle diagram showing an outline of cutting process evaluation system 1 according to an embodiment of the present disclosure. In FIG. 1, cutting process evaluation system 1 according to the present disclosure includes input processor 2 that executes an input step, learning processor 3 that executes a learning step, and output processor 4 that executes an output step, as functions. Cutting process evaluation system 1 may further include sensor 150 that measures a physical quantity related to the cutting process. Sensor 150 includes at least one of load sensor 151, sound sensor 152, position sensor 153, and temperature sensor 154, which will be described later.

Input processor 2 acquires physical quantity 15 measured during the cutting process as state variable 12, and inputs the state variable to evaluation model 11 (described later) of learning processor 3.

Learning processor 3 includes learned evaluation model 11 and data set group 14. Learning device 21 includes input processor 2 and learning processor 3.

Output processor 4 outputs cutting evaluation result 13.

With such a configuration, cutting process evaluation system 1 is configured to input state variable 12 to learned evaluation model 11 and output cutting evaluation result 13. Evaluation model 11 is optimized through a learning step by learning processor 3 using data set group 14. Cutting evaluation result 13 is a result of predicting the presence or absence of an abnormality in the cutting process when physical quantity 15 is measured and the cause at the time of the abnormality.

Input state variable 12 includes at least one of a cutting load, a sound generated during the cutting process, a vibration generated during the cutting process, a shear rate during the punching process, a clearance between the die and the punch, and a temperature of the workpiece generated during the cutting process (hereinafter referred to as "processing temperature"). Physical quantity 15 measured in real time from the start to the end of one cutting process is converted as necessary and input to evaluation model 11 as state variable 12. Since a sufficient number of samples is required to grasp the characteristics of the process, for example, the tendency of the local value of physical quantity 15 such as the curvature of the load profile curve in the cutting evaluation, a sampling period (measurement period) of physical quantity 15 is desirably 1/100 or less of the time required for cutting.

State variable 12 based on physical quantity 15 is input to evaluation model 11. Evaluation model 11 is a model provided with a function for processing input state variable 12 to convert the state variable into an output (that is, a function for obtaining and outputting cutting evaluation result 13 based on state variable 12). By optimizing the function in learning processor 3 described later with reference to FIG. 2, evaluation model 11 can obtain cutting evaluation result 13 with high accuracy.

Cutting evaluation result 13 is a stepwise evaluation of abnormalities in the cutting process, and is classified into an n+1 patterns that is the sum of one pattern when there is no abnormality in the process and n patterns, the number of patterns of the causes of abnormality, when there is an abnormality in the process. Examples of patterns of the causes of abnormality include known defect causes such as excess clearance, insufficient clearance, tool wear, and installation error of a mold.

Specifically, cutting evaluation result 13 is a one-dimensional vector that holds a probability of the pattern for each of n+1 elements, and output processor 4 outputs the element having the largest value among the elements, that is, the pattern having the highest probability of occurrence (defect cause).

Data set group 14 used for learning evaluation model 11 is accumulated as a set of two pieces of data, input data and output data. Specifically, data set group 14 is accumulated as a set, state variable 12 based on physical quantity 15 measured in one cutting process as input data, and cutting result 16 (see FIG. 2) when state variable 12 is measured as output data, for each cutting process.

State variable 12 is a variable based on physical quantity 15 obtained by actual measurement for each process. As state variable 12, physical quantity 15 may be acquired as it is, but it is preferable to acquire a value obtained by converting physical quantity 15. For example, in order to measure the cutting load that is an example of physical quantity 15 as will be described later with reference to FIG. 7, when the load is measured by load sensor 151 shown in FIG. 7 to be described later, the detected load includes a load by stripper 107 in addition to the cutting load. Therefore, the load by stripper 107 is calculated from a spring constant of a spring included in stripper 107 and an approximate line of a linear load. Then, the cutting load is calculated by removing the load by stripper 107 from the load measured by load sensor 151. Thus, only the calculated load, that is, the cutting load is acquired as state variable 12.

That is, the information acquired as physical quantity 15 may include information other than information necessary for the cutting process evaluation. Therefore, as state variable 12, it is preferable to acquire a value obtained by appropriately converting physical quantity 15.

Cutting result 16 is obtained by actual measurement for each process and is associated with physical quantity 15 during cutting. That is, when a certain process is performed, detection of physical quantity 15 and determination of cutting result 16 are performed as a set, and the set is input to data set group 14. Cutting result 16 is determined by a person or mechanical means using the related art as the quality of the processed product and is input to data set group 14, for example. Cutting result 16 is measured by a device that actually measures the cutting result and is input as a signal, for example. Cutting result 16 may be evaluated by a person in an inspection process and may be input via an input device such as a keyboard, for example. The quality of the processing process is most easily determined based on the quality of the processed product, but the quality of the processing process may be determined based on other references.

Cutting result 16 is a stepwise evaluation of abnormalities in the cutting process, and is classified into an n+1 patterns that is the sum of one pattern when there is no abnormality in the process and n patterns, the number of patterns of the causes of abnormality, when there is an abnormality in the process. Examples of types of the causes of abnormality include defect causes such as clearance deviation, tool wear, chipping, burr height, clogging, and installation error of a mold.

An example of cutting result 16 in which the abnormalities in the cutting process are classified stepwise will be described with reference to FIG. 11. FIG. 11 is a diagram showing an example of cutting result 16. In the example shown in FIG. 11, as the cause of abnormality, the size of tool wear, the maximum chipping width, the burr height, the clogging, and the size of clearance deviation are evaluated. As shown in FIG. 11, the degree of each cause of abnormality is classified into three stages and is denoted as labels 1 to 3. That is, label 1 indicates that there is no abnormality, label 2 indicates a yellow signal, that is, attention is required, and label 3 indicates that there is an abnormality.

Specifically, when the tool wear is less than R20 μm, it is evaluated as no abnormality and label 1 is attached. When the tool wear is R20 μm or more and less than R25 μm, it is evaluated as a yellow signal and label 2 is attached. When the tool wear is R25 μm or more, it is evaluated as abnormal and label 3 is attached. Further, when there is no clogging or substantially no clogging, it is evaluated as no abnormality and label 1 is attached. When there is substantially clogging, it is evaluated as abnormal and label 3 is attached. Here, the wording that there is substantially no clogging or substantially clogging indicates that there is no clogging or substantially clogging to the extent that it causes abnormalities.

In the example shown in FIG. 11, the size of tool wear, the maximum chipping width, the burr height, and the size of clearance deviation are evaluated by numerical values (scalar), and are classified stepwise based on the numerical values. However, the present disclosure is not limited thereto. For example, tool wear, chipping, burrs, and clearance deviation may be evaluated in two stages (presence or absence of an abnormality due to each cause of the abnormality). Further, cutting result 16 may be the numerical values of the size of tool wear, the maximum chipping width, the burr height, and the size of clearance deviation.

That is, cutting result 16 represents the degree of abnormality in the cutting process stepwise or numerically for each type of the causes of abnormality. Cutting result 16 may include at least one type of the causes of abnormality.

Figure 2:
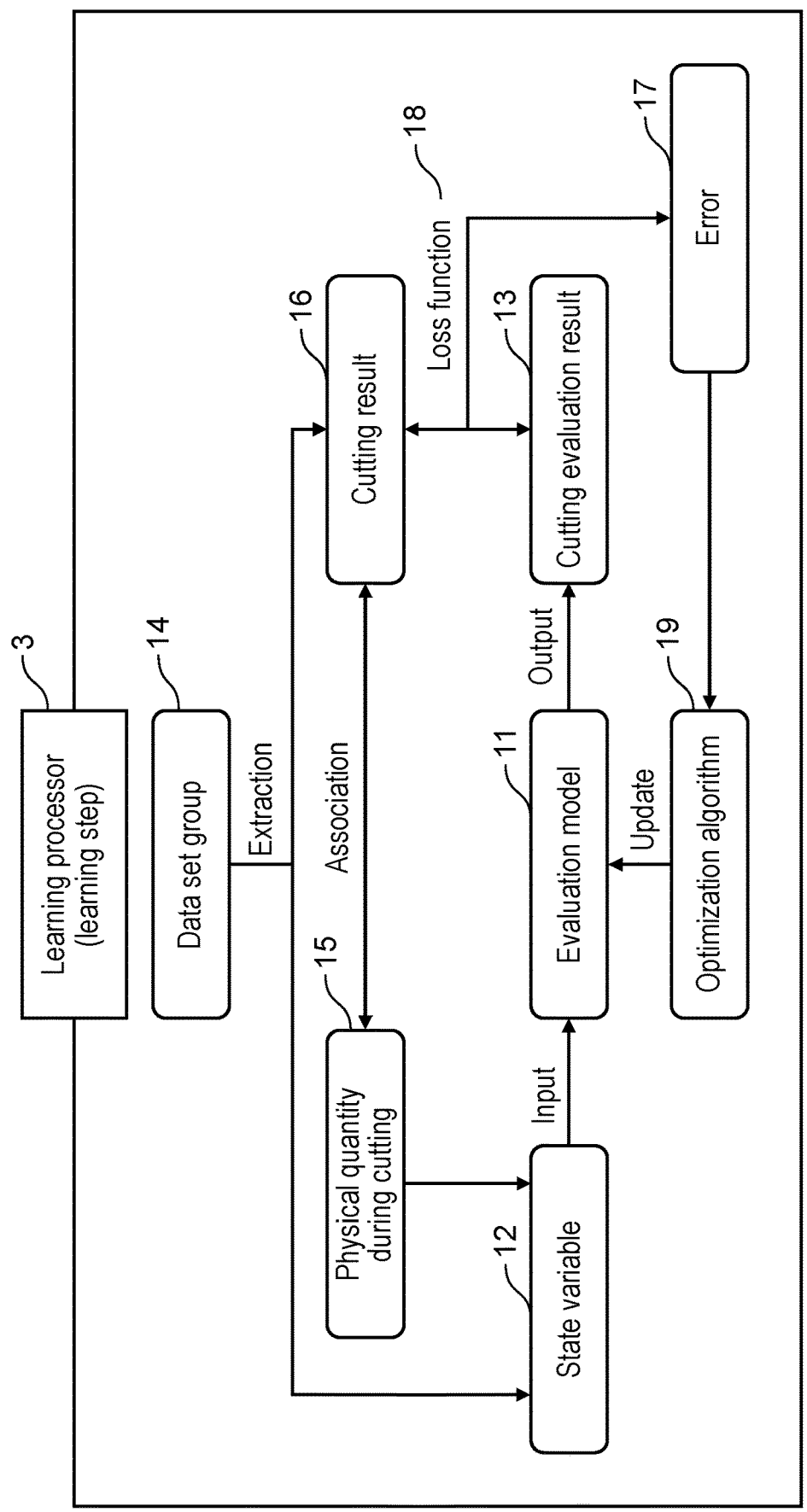
FIG. 2 is a block principle diagram showing an outline of a learning process in the cutting process evaluation system used in the embodiment of the present disclosure.

FIG. 2 is a block principle diagram showing an outline of learning steps performed by learning processor 3 of evaluation system 1 used in the embodiment of the present disclosure. Of the data sets (state variable 12 and cutting result 16) extracted from data set group 14, input data, that is, state variable 12 based on physical quantity 15 during the cutting is input to evaluation model 11. Error 17 between cutting evaluation result 13 output from evaluation model 11 and cutting result 16 extracted from data set group 14 is calculated by loss function 18. Then, the weighting coefficient of evaluation model 11 is updated by optimization algorithm 19 based on error 17. The update of the weighting coefficient by this series of operations is performed using all the data sets accumulated in data set group 14. Specifically, learning is performed by repeatedly updating the weighting coefficient of evaluation model 11 using entire data set group 14 until error 17 which is the sum of the difference between total cutting result 16 in entire data set group 14 and cutting evaluation result 13 estimated by evaluation model 11 is minimized and converged. As loss function 18 suitable for the derivation of error 17, since evaluation model 11 classifies the causes of abnormality for each pattern and outputs cutting evaluation result 13 as described above, it is desirable to use cross-entropy error, which is a loss function suitable for group classification algorithms. As a technique used for optimization algorithm 19, it is desirable to use the steepest descent method or RMSprop.

Here, a specific error calculation method will be described using the example of cutting result 16 shown in FIG. 11. As shown in FIG. 11, when cutting result 16 includes a plurality of causes of abnormality, a plurality of evaluation models 11 respectively associated with the plurality of causes of abnormality are used. That is, the same number of evaluation models 11 as the types of the causes of abnormality are used.

As shown in FIG. 11, when cutting result 16 is evaluated stepwise, cutting result 16 and cutting evaluation result 13 are represented by the probability that an event of each label occurs. For example, when cutting result 16 (actually measured value) for a certain cause of abnormality is label 1, cutting result 16 is represented by [1 0 0]. Further, in cutting evaluation result 13 (predicted value) for a certain cause of abnormality, when the probability of label 1 is 0.2, the probability of label 2 is 0.7, and the probability of label 3 is 0.1, cutting evaluation result 13 is represented by [0.2 0.7 0.1].

When cutting result 16 is evaluated stepwise, as described above, the cross-entropy error of the following Equation (1) is used as loss function 18. When the above actually measured value [1 0 0] and predicted value [0.2 0.7 0.1] are obtained, error 17 is calculated using the following Equation (1) as shown in the following Equation (2).

$$E = -\Sigma_k t_k \log(y_k) \qquad \text{Equation (1)}$$

$$E = -(1 \log 0.2 + 0 \log 0.7 + 0 \log 0.1) \qquad \text{Equation (2)}$$

When cutting result 16 is evaluated numerically, the mean square error shown in the following Equation (3) may be used as loss function 18. For example, when the actually measured value of the burr height is 13 μm and the predicted value thereof is 18 μm, error 17 may be calculated using the following Equation (3) as shown in the following Equation (4). Instead of the mean square error, another function that can derive an error between two scalar values may be used.

$$E = \tfrac{1}{2}\Sigma_k(y_k - t_k)^2 \qquad \text{Equation (3)}$$

$$E = \tfrac{1}{2}(18-13)^2 \qquad \text{Equation (4)}$$

As described above, error 17 is calculated for each type of the causes of abnormality, and the weighting coefficient of evaluation model 11 associated with each cause of abnormality is updated by optimization algorithm 19 based on calculated error 17.

The learning step can be performed in parallel with the process. That is, optimization of evaluation model 11 can be advanced by learning in real time during the process. However, data set group 14 requires cutting result 16 obtained by actual measurement. Therefore, it is preferable to perform the learning step after the end of the cutting process, which is the timing at which input state variable 12 and cutting result 16 obtained by the actual measurement are obtained.

In order to effectively optimize evaluation model 11 by the learning step, it is necessary to have a strong connection (correlation) between input data and output data of data set group 14. In optimizing evaluation system 1, it is required to appropriately select state variable 12 based on physical quantity 15 having a strong correlation with the processing abnormality as an input. As an example of state variable 12 having a strong correlation with the processing abnormality, a correlation between the cutting load and the processing quality, a correlation between a sound generated during the cutting process and the processing quality, and a correlation between the processing temperature and the processing quality will be described below.

Figure 3:
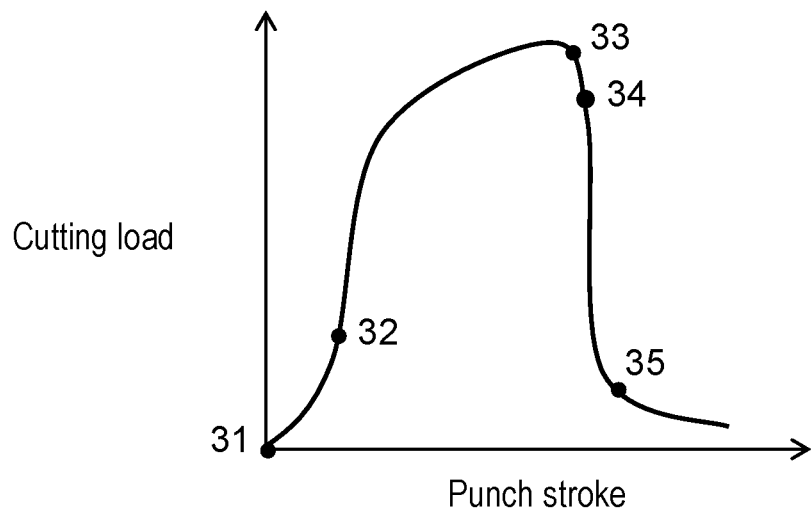
FIG. 3 is a general cutting load-punch stroke diagram illustrating the correlation between a load and a processing quality used in the embodiment of the present disclosure.

FIG. 3 is a general cutting load-punch stroke diagram illustrating the correlation between a cutting load (shear load) and a processing quality used in the embodiment of the present disclosure. The cutting load-punch stroke diagram is a diagram in which the vertical axis represents the shear load generated when cutting the workpiece and the horizontal axis represents the punch stroke when cutting the workpiece. This cutting load-punch stroke diagram shows that there are five processes in the transition of the cutting load.

The section from point 31 to point 32 in FIG. 3 is generally referred to as a compressive deformation process, where the workpiece is compressed by the punch and the die, the shear drop occurs, and the workpiece bites into both the die and punch tools. For example, when the tool is worn, it is expected that a large punch stroke (hereinafter, also simply referred to as "stroke") is required to move to the next shear deformation process with less biting into the workpiece.

The section from point 32 to point 33 in FIG. 3 is generally referred to as a shear deformation process, where slip deformation occurs in the workpiece, resulting in bending of the workpiece, and bending moment and tensile force are generated in the workpiece. Generally, the larger the clearance between the die and the punch (hereinafter, when simply referred to as "clearance", it is assumed that it means the clearance between the die and the punch), the greater the bending moment generated in the workpiece. Therefore, when the clearance is excessively large, it is expected that the cutting load increases due to the strong bending moment generated in the workpiece in this section acting on the inner wall (die hole) of the die. Conversely, when the clearance is too small, it is expected that the bending moment acting on the inner wall of the die decreases and the cutting load decreases.

The section from point 33 to point 34 in FIG. 3 is generally referred to as a crack growth process, where the crack is generated in the workpiece and the shear load starts to decrease. Generally, the larger the clearance, the earlier the crack generation time. Therefore, when the clearance is excessively large, it is expected that the punch stroke until reaching this section is smaller than usual. That is, when the clearance is excessively large, the crack growth process is reached with a small stroke.

The section from point 34 to point 35 in FIG. 3 is generally referred to as a fracture separation process, where cracks that have developed from both tools (punch and die) sides of the workpiece meet to separate (fracture) the workpiece. Generally, when the clearance is small, the cracks may stop and secondary shearing may occur. Accordingly, when the clearance is too small, secondary shearing occurs. Therefore, it is expected that the diagram has a plurality of inclinations in this section.

The section after point 35 in FIG. 3 is a process in which the punch passes through the die after the cutting process is completed. When the cutting dust of the workpiece adheres to the punch or die, or when the punch and die are misaligned and the punch is in contact with the die, it is expected that the cutting load still remains despite the workpiece being punched.

Further, the stroke amount of the punch in the section from point 31 to point 35 in FIG. 3 is expected to correlate with the workpiece thickness. When the workpiece thickness is thicker than expected, the stroke amount from point 31 to point 35 is expected to increase, and when the workpiece thickness is thinner than expected, the stroke amount from point 31 to point 35 is expected to decrease. Therefore, it is expected that an abnormality due to a workpiece thickness difference can be detected from the stroke amount of the punch, for example.

Figure 4:
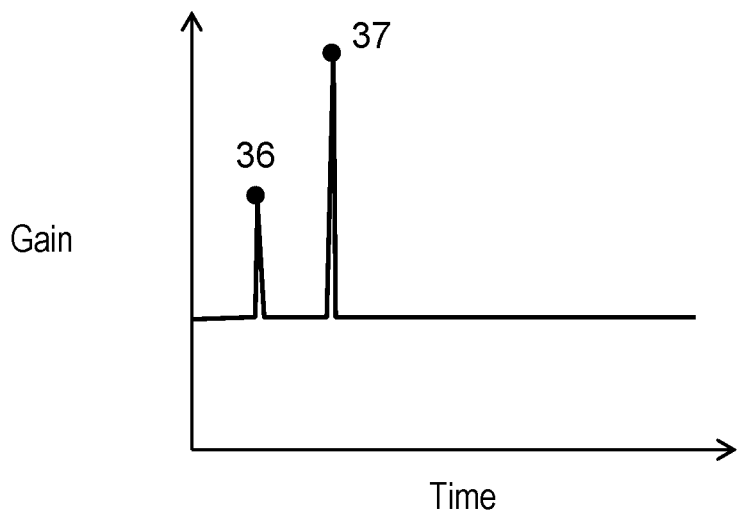
FIG. 4 is a general sound-time diagram illustrating the correlation between a sound and a processing quality used in the embodiment of the present disclosure.

FIG. 4 is a general sound-time diagram illustrating the correlation between a sound generated during the cutting process (processing sound) and a processing quality used in the embodiment of the present disclosure. The vertical axis represents the gain of the processing sound generated when cutting the workpiece and the horizontal axis represents the time from the point when the punch member starts to move, which indicates the presence of two peaks in the cutting process. The peak of point 36 is a peak due to a sound generated at the moment when the stripper presses the workpiece, and the peak of point 37 is a peak due to a sound generated when the workpiece is pushed and cut by the punch, that is, between the time when the punch contacts the workpiece and the time when the cutting of the workpiece is completed.

When there is a peak between point 36 and point 37, the punch is in sliding contact with the wall surface that defines the guide for guiding the punch provided in the stripper, and it is expected that the wear of the punch progresses early.

When the peak of point 37 is high, there is a high possibility that the workpiece has cracked, and it is expected that the workpiece is a defective product.

When there is a peak after point 37, the punch is rubbed against the inner wall (die hole) of the die, and it is expected that the wear of the punch and the die progresses early.

Figure 5:
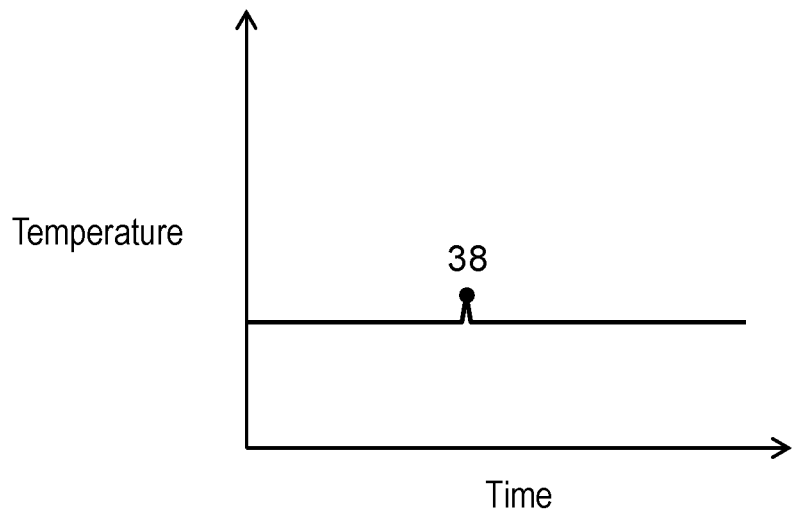
FIG. 5 is a general temperature-time diagram illustrating the correlation between a temperature and a processing quality used in the embodiment of the present disclosure.

FIG. 5 is a general processing temperature-time diagram illustrating the correlation between a temperature and a processing quality used in the embodiment of the present disclosure. The vertical axis represents the processing temperature generated when cutting the workpiece, and the horizontal axis represents the time from the start of the processing, where a peak of point 38 occurs in the processing temperature only at the time of cutting (that is, from when the punch contacts the workpiece to when the cutting of the workpiece is completed).

When the peak of point 38 at the processing temperature is high, the energy required for the processing is high, so that an excessive load is applied to the punch and the die, and it is expected that the life of the punch and the die is reduced early.

As described above, by grasping the characteristics of the cutting load-punch stroke diagram, processing sound-time diagram, and processing temperature-time diagram, it can be expected that the presence or absence and cause of abnormality in the cutting process can be specified. Therefore, evaluation model 11 in cutting process evaluation system 1 is desirably a model that can grasp the characteristics of state variable 12 (cutting load, processing sound, processing temperature, and the like), and preferably, it is desirable to use a model of a convolutional neural network applied to an image recognition algorithm.

Figure 6:
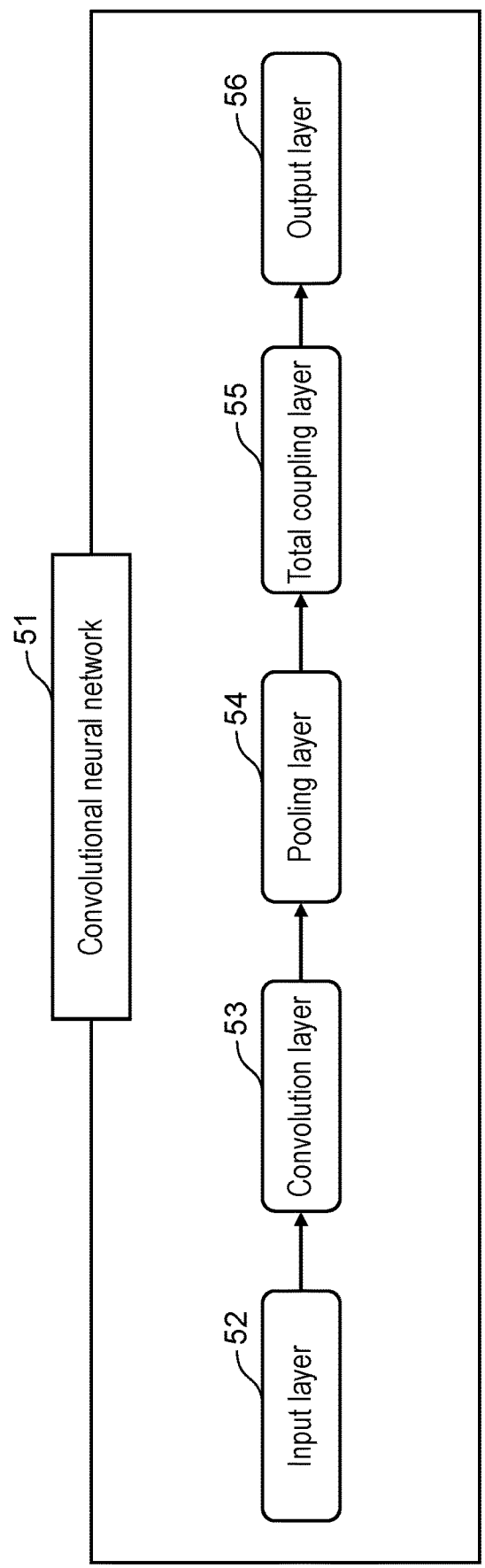
FIG. 6 is a configuration diagram of a convolutional neural network used in the embodiment of the present disclosure.

FIG. 6 is a configuration diagram of convolutional neural network 51 applied to evaluation model 11 in the embodiment of the present disclosure. First, state variable 12 is input to input layer 52, and in convolution layer 53, for example, in the cutting load-punch stroke diagram shown in FIG. 3, the operation of grasping the characteristics of local data of state variable 12, such as the curvature of the section curve of the compressive deformation process shown from point 31 to point 32 or the slope of the fracture separation process shown from point 34 to point 35 is repeated at various target data and data positions. Thus, the characteristics of entire state variable 12 are extracted by convolution layer 53. Next, processing is performed in pooling layer 54 so that the characteristics extracted by convolution layer 53 become prominent. Finally, classification is performed in total coupling layer 55 by using the characteristics summarized in pooling layer 54, and the result is output to output layer 56.

As described above, convolutional neural network 51 is a model that is good at grasping and classifying the characteristics of input data. Therefore, by applying convolutional neural network 51 to evaluation model 11 described with reference to FIG. 3, there are effects that the ability to grasp the characteristics of state variable 12 is improved, and the accuracy of cutting evaluation result 13 as an output is greatly improved.

Figure 7:
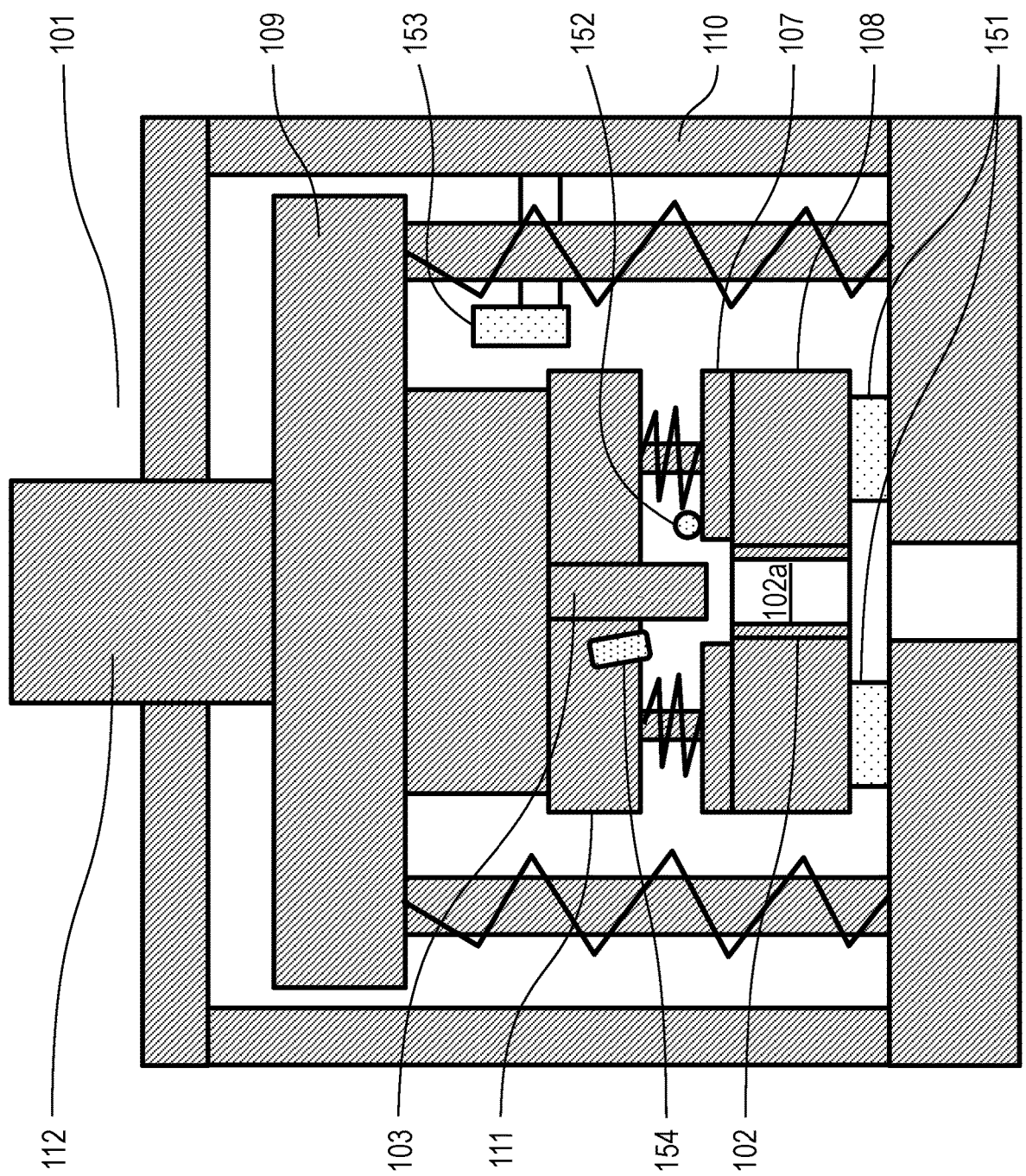
FIG. 7 is an overall diagram showing an outline of a cutting device to which the cutting process evaluation system used in the embodiment of the present disclosure is applied.

FIG. 7 is an overall diagram showing an outline of cutting device 101 to which cutting process evaluation system 1 used in the embodiment of the present disclosure is applied. In cutting device 101, a workpiece (not shown) is placed on die 102 and is punched into the inner diameter (die hole 102a) of die 102 by the descending punch 103 while being pressed by stripper 107. In cutting device 101, load sensor 151, sound sensor 152, position sensor 153, and temperature sensor 154 are installed as sensors for measuring physical quantity 15 generated when the workpiece is cut. Cutting process evaluation system 1 is configured by including these sensors 151, 152, 153, and 154 and controller 112 described later.

Load sensor 151 preferably measures the load (cutting load) by which punch 103 pushes out the workpiece placed on die 102 with high sensitivity. Therefore, it is desirable to install load sensor 151 immediately below base 108 on which die 102 is installed. Specifically, the number of load sensors 151 is preferably 2 to 4, and the optimal number of load sensors 151 is 3 because the cutting load is surely distributed to all load sensors 151. As the position of load sensor 151, it is desirable that load sensors 151 are arranged at equal intervals and even a part of load sensor 151 does not protrude from the lower surface of base 108. As load sensor 151, since measurement at a high speed (measurement with a quick response) is desirable, a quartz piezoelectric sensor is desirable, and a three-component load sensor that can measure the cutting load not only in the vertical direction but also in the horizontal direction is more desirable.

Since it is desirable that sound sensor 152 does not sense any sound other than the sound generated at the time of cutting, it is desirable to install sound sensor 152 immediately above stripper 107. As a specific position of sound sensor 152, it is desirable that sound sensor 152 does not protrude from the upper surface of stripper 107 because punch 103 is close. As sound sensor 152, a microphone having a diameter of 6 mm or less or an acoustic emission (AE) sensor is desirable because the space on stripper 107 is narrow.

Position sensor 153 measures the lowering amount of upper base 109 and furthermore, the punch stroke. It is desirable to install position sensor 153 at a location that is not easily affected by vibrations generated during the cutting process. Therefore, it is desirable to install position sensor 153 inside device cover 110. Specifically, it is desirable to install position sensor 153 at a position 0.5 mm inward from upper base 109 in a state where punch 103 is located at the bottom dead center. As position sensor 153, a non-contact capacitive sensor is desirable in consideration of the possibility that upper base 109 is made of a non-metallic material in measuring the position of the descending member (upper base 109).

Temperature sensor 154 preferably measures the processing temperature near punch 103. Therefore, it is desirable that temperature sensor 154 is installed in a form embedded in punch plate 111 so that a sensor tip thereof (detection end) faces the processing point (in other words, die hole 102a). Specifically, in order to prevent contact with stripper 107 during the cutting process, temperature sensor 154 is preferably disposed so that the length of the tip of temperature sensor 154 protruding from the lower surface of punch plate 111 is within 5 mm. When temperature sensor 154 is a radiation type thermometer, it is desirable that the angle of temperature sensor 154 with respect to the vertical direction is within 10 degrees in order to accurately measure the processing temperature. Since temperature sensor 154 is installed in the vicinity of punch 103 in an extremely narrow space, it is necessary to prevent temperature sensor 154 and punch 103 from contacting each other during the cutting process. Therefore, temperature sensor 154 is desirably a radiation type temperature sensor.

Cutting device 101 further includes controller 112. Controller 112 has a function as a learning device of cutting process evaluation system 1.

Figure 8:
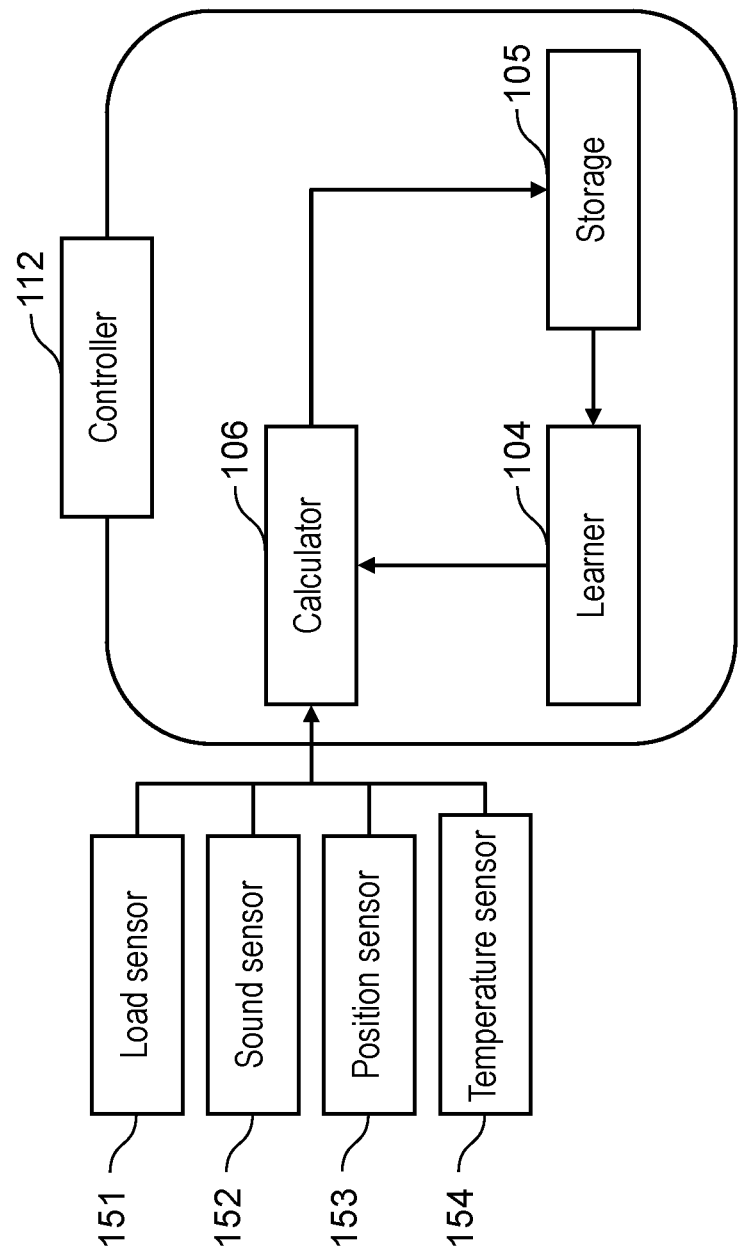
FIG. 8 is a functional block diagram related to a controller according to the embodiment of the present disclosure.

Controller 112 will be described with reference to FIGS. 1 and 8. FIG. 8 is a functional block diagram related to controller 112 according to the embodiment of the present disclosure.

As shown in FIG. 8, controller 112 includes learner 104, storage 105, and calculator 106.

Calculator 106 acquires state variable 12 based on information (physical quantity 15) acquired from each of load sensor 151, sound sensor 152, position sensor 153, and temperature sensor 154 at the time of cutting. That is, calculator 106 has a function as input processor 2 shown in FIG. 1. Calculator 106 outputs cutting evaluation result 13 by using evaluation model 11. That is, calculator 106 has a function as output processor 4. After cutting the workpiece, state variable 12 input to calculator 106 at the time of cutting and cutting result 16 are sequentially accumulated in storage 105 as a data set. That is, storage 105 has a function as data set group 14. Learner 104 executes learning of evaluation model 11 based on all data sets (data set group 14) accumulated in storage 105, and feeds back the learned evaluation model 11 to calculator 106. That is, learner 104, storage 105, and calculator 106 function as learning processor 3 in cooperation.

Figure 9:
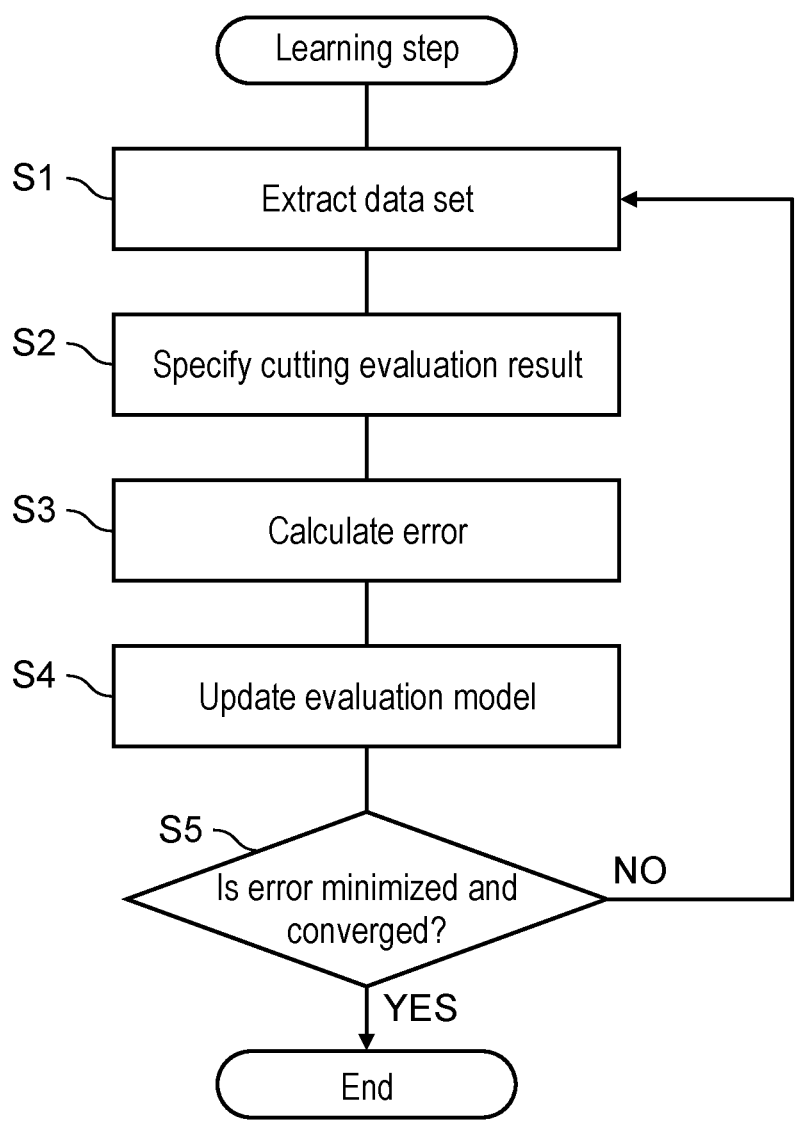
FIG. 9 is a flowchart showing learning steps executed by a learning device according to the embodiment of the present disclosure.

FIG. 9 is a flowchart showing learning steps executed by learning device 21 according to the present embodiment. As shown in FIG. 9, learning processor 3 extracts a data set in which state variable 12 and cutting result 16 are associated from data set group 14 (S1). Learning processor 3 specifies cutting evaluation result 13 for state variable 12 included in the extracted data set by using evaluation model 11 (S2). Learning processor 3 calculates an error from cutting result 16 included in the extracted data set and specified cutting evaluation result 13 (S3). Learning processor 3 updates evaluation model 11 based on the calculated error (S4). Learning processor 3 determines whether or not the calculated error is minimized and converged (S5). When the error is not minimized and converged (NO in S5), learning processor 3 executes the processes of S1 to S4 again. Meanwhile, when the error is minimized and converged, learning processor 3 ends the learning step.

Figure 10:
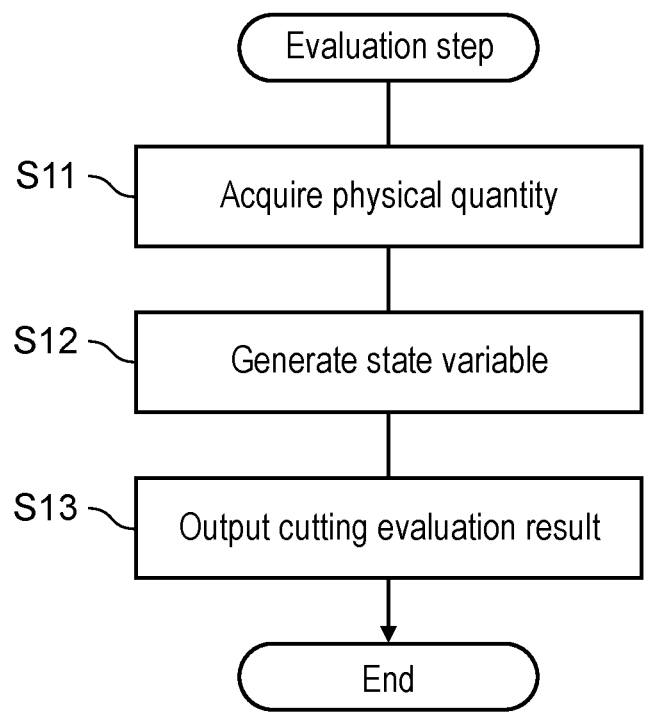
FIG. 10 is a flowchart showing evaluation steps executed by the cutting process evaluation system according to the embodiment of the present disclosure.

FIG. 10 is a flowchart showing evaluation steps executed by cutting process evaluation system 1 according to the present embodiment. As shown in FIG. 10, input processor 2 acquires physical quantity 15 measured by respective sensors 151 to 154 (S11). Input processor 2 generates state variable 12 based on the acquired physical quantity 15 (S12). Output processor 4 outputs cutting evaluation result 13 obtained by inputting state variable 12 to evaluation model 11 (S13).

The cutting process evaluation system of the present disclosure includes a sensor that measures a physical quantity related to a cutting process, a learning device, and an output processor that derives the evaluation using the evaluation model updated by the learning device.

According to the learning device and the cutting process evaluation system of the present disclosure, it is possible to evaluate the processing quality using the evaluation model by using the state variable based on the physical quantity related to the cutting process, and further update the evaluation model. Accordingly, the processing quality can be evaluated with high accuracy.

According to the present disclosure, it is possible to predict the processing abnormality without depending on skill level by updating the evaluation model while accurately evaluating the processing quality using the evaluation model. Therefore, it is expected that the number of defects is reduced by early response to abnormalities, and productivity is improved by reducing the downtime of the device.

What is claimed is:

1. A learning device comprising:
an input processor; and
a learning processor,
wherein
the input processor acquires a physical quantity related to a cutting process, and inputs a state variable based on the physical quantity, as an input into an evaluation model, to the learning processor,
the learning processor calculates an error between a cutting evaluation result and a measured cutting result by executing a loss function,
the cutting evaluation result is an output from the evaluation model,
the learning processor uses the error as an input into an optimization algorithm and executes the optimization algorithm to update a weighting coefficient of the evaluation model,
the cutting evaluation result is a result of predicting presence or absence of an abnormality in the cutting process and a cause at the time of the abnormality, when a physical quantity is measured,
the cutting result is a stepwise evaluation of the abnormality in the cutting process,
the error is calculated using a cross-entropy error, and
steepest descent method or RMSprop is used as a technique used for optimization algorithm.

2. The learning device of claim 1,
wherein the cutting process is a punching process in which a workpiece is punched with a punch, and
the input processor acquires, as the state variable, at least one of a load acting on the workpiece during the punching process, a sound generated by the punching process, a vibration generated by the punching process, a shear rate during the punching process, a clearance between the punch and a die, and a temperature of the workpiece during the punching process.

3. A cutting process evaluation system comprising:
a sensor that measures a physical quantity related to a cutting process;
the learning device of claim 1; and
an output processor that derives the cutting evaluation result by using the evaluation model updated by the learning device.

4. The cutting process evaluation system of claim 3,
wherein the cutting process is a punching process in which a workpiece is punched with a punch, and
the sensor includes at least one of a load sensor that measures a load acting on the workpiece during the punching process, a sound sensor that measures a sound generated by the punching process, and a position sensor that measures a position of the punch.

* * * * *